United States Patent [19]
Nakabayashi et al.

[11] Patent Number: 5,658,561
[45] Date of Patent: Aug. 19, 1997

[54] METHOD OF PRODUCING ANTI-THROMBOGENIC MATERIAL AND MATERIAL PRODUCED THEREBY

[75] Inventors: Nobuo Nakabayashi; Kazuhiko Ishihara, both of Tokyo, Japan

[73] Assignee: Biocompatibles Limited, Uxbridge, England

[21] Appl. No.: 284,685

[22] PCT Filed: Feb. 12, 1993

[86] PCT No.: PCT/GB93/00298

§ 371 Date: Jan. 24, 1995

§ 102(e) Date: Jan. 24, 1995

[87] PCT Pub. No.: WO93/15775

PCT Pub. Date: Aug. 19, 1993

[30] Foreign Application Priority Data

Feb. 13, 1992 [JP] Japan .................. 4-058762

[51] Int. Cl.[6] .............. A61K 31/765; A61K 31/74; A61K 47/48; A61F 2/02
[52] U.S. Cl. .................. 424/78.37; 424/78.17; 424/424
[58] Field of Search .............. 424/424, 78.17, 424/78.37

[56] References Cited

U.S. PATENT DOCUMENTS 5,368,733  11/1994  Nakabayashi et al. .
5,453,467   9/1995  Bamford et al. .

FOREIGN PATENT DOCUMENTS

| 0266795 | 5/1988 | European Pat. Off. . |
| 0425200 | 5/1991 | European Pat. Off. . |
| 0580871 | 2/1994 | European Pat. Off. . |
| 0013639 | 9/1991 | United Kingdom . |
| 0001846 | 4/1992 | United Kingdom . |
| WO9113639 | 9/1991 | WIPO . |
| WO9206719 | 4/1992 | WIPO . |
| WO9207858 | 5/1992 | WIPO . |

OTHER PUBLICATIONS

Shirakawa et al., "Preparation of Epoxy Resins Containing Phosphate Zwitterionic Group", Jpn. Kokai, Tokkykoho, 8 pp. (Abstract Only).

Ishihara et al., "Improvement of Blood Compatibility on Cellulose Dialysis Membrane", Biomaterials, 13(1992) No. 3, pp. 145–149; No. 4, pp. 235–239.

Kishida, et al., Biomaterials 13 (1992), No. 2, "Interactions of poly(ethylene glycol)–grafted cellulose membranes with proteins and platelets", pp. 113–118.

Ishihara, et al., Journal of Biomedical Materials Research, vol. 25, No. 11, Nov. 1991 "Protein adsorption from human plasma is reduced on phospholipid polymers" pp. 1397–1407.

Primary Examiner—Carlos A. Azpuru
Attorney, Agent, or Firm—Sughrue, Mion, Zinn, Macpeak & Seas

[57] ABSTRACT

A method of producing a material bearing zwitterionic groups, such as phosphoryl choline groups, which comprises treating at least the surface of a substrate with a solution or dispersion of a polymer grafter with zwitterionic groups, and material produced by the method. The method is suitable for producing materials for use in contact with blood and in particular a regenerated cellulose membrane.

26 Claims, 2 Drawing Sheets

COMPARATIVE EXAMPLE 1

COMPARATIVE EXAMPLE 1

EXAMPLE 16

COMPARATIVE EXAMPLE 3

EXAMPLE 18

METHOD OF PRODUCING ANTI-THROMBOGENIC MATERIAL AND MATERIAL PRODUCED THEREBY

The present invention relates to a method of producing a material having improved anti-thrombogenicity, to certain materials produced thereby and in particular a regenerated cellulose membrane which is particularly suitable for use in artificial kidneys. The invention further provides a device such as a contact lens, biomedical or blood-contacting device or filtration membrane comprising such a material.

At present, methods for prolonging the lives of patients with chronic renal insufficiency include blood dialysis, blood filtration and other blood-purification methods. In Japan, more than 100.000 patients are treated with such blood-purification methods.

The principles of blood purification involve bringing the blood and a dialysate into contact via a membrane, allowing the diffusion of the waste products and the metabolic products contained in the blood into the dialysate and their subsequent removal, and removing the water surplus by taking advantage of the pressure differences.

As is generally known, regenerated cellulose membranes, especially cellulose membranes regenerated by the copper ammonium method, are commonly used in the method of artificial dialysis in particular, with progress in dialyzers and dialysis techniques, they have come to play an important role in the life prolongation and social recovery of patients with renal insufficiency; this is because the regenerated cellulose membrane is characterized not only by a superior dialysis capacity and mechanical strength, but also by high safety confirmed by years of experience.

Despite the process in dialysis methods, however, various problems associated with dialysis have still remained unsolved. One of these is the problem of various side effects which are believed to result from the long-term administration of high doses of anticoagulants.

Currently, in cases in which artificial dialysis is conducted, anticoagulants such as heparin are continuously administered in order to suppress the blood clotting reaction in the artificial dialyzer. Despite current improvements in the removal of solute in artificial dialyzers, as well as the possibility of achieving long-term life prolongation of up to 20 years, a number of problems caused by the use of heparin have been pointed out continuously. In particular, it has become apparent that long-term administration of heparin produces in patients side effects such as liver disorders and other lipid metabolic disorders, and prolongs the bleeding time and allergic reactions.

As a result of the above-mentioned points, there has been strong demand for the development of an artificial dialyzer which will not cause blood clotting, even with reduced doses of anticoagulants administered during the artificial dialysis, or with no anticoagulants at all. In addition, the manufacture of anti-thrombogenic dialyzers which are completely portable is expected to considerably facilitate home treatments, which will promote the social recovery of patients who [otherwise] would have to be restricted to a hospital for approximately five hours every two or three days of the week.

It has been suggested that some membranes made of synthetic macromolecules have excellent anti-thrombogenicity; but membranes made of synthetic macromolecules have low mechanical strength and are susceptible to the formation of pinholes, they are of limited use in sterilization methods due to insufficient heat resistance, and they lack balanced performance, i.e., the balance between water permeability and substance permeability, so that there are many disadvantages in terms of practical use.

On the other hand, methods have been offered for improving the anti-thrombogenicity of regenerated cellulose membranes, without sacrificing their other excellent properties. For example, a method of imparting anti-thrombogenicity by heparinizing the membrane surface was offered in Japanese Laid-Open Patent Application 51-194, but since no satisfactory results could be obtained, and the cost of such a method was high, it has not been applied.

The attempts made so far to improve regenerated cellulose membranes have focused mainly on transient leukopenia and the suppression of the complement activation occurring when blood dialysis is conducted using a regenerated cellulose membrane. Such methods as fixing macromolecules containing tertiary amino groups or covalently bonding hydrophilic macromolecular chains such as polyethylene oxide chains to the membrane surface have been reported, but the suppression of blood clotting has remained unsatisfactory.

In light of the above, the present invention seeks to provide a regenerated cellulose membrane with improve anti-thrombogenicity. More generally, it further seeks to provide other materials with improved anti-thrombogenicity or which are subject to reduce adhesion of protein when exposed to protein containing solutions. The invention further seeks to provide an improved process for producing such materials.

It is worth mentioning that attempts have also been made to use phospholipid polar groups in order to obtain an anti-thrombogenic material; for example, 2-methacryloyloxyethyl phosphorylcholine (MPC) was offered in Japanese Laid-Open Patent Application 54-63025.

It is believed that macromolecules comprising the phospholipid polar group phosphorylcholine group effectively suppress blood clotting because their macromolecular surface resembles that of biological membranes, because plasma proteins do not adhere to the surface, and because they do not induce adherence or activation of thrombocytes (*Biological Materials*, 8:231–237 (1990), *J. Biomed. Mater/Res.*, 25:1397–1407 (1991)). As disclosed in Japanese Laid-Open Patent Application 3-39309, the anti-thrombogenicity of the copolymer of such a polymerizable monomer with methacrylate and styrene is especially superior, and a method of fixing said copolymer to a regenerated cellulose membrane has also been considered.

One fixing method is the coating method, but coating a hydrophilic base such as a regenerated cellulose membrane with a different macromolecule for a surface treatment has involved many problems, such as shedding and elution of the treatment macromolecule.

On the other hand, the method of bringing about a reaction between a base and a macromolecular chain and then conducting grafting is effective from the perspective of avoiding such shedding and elution; such commonly-known techniques include the technique of conducting graft polymerization of MPC and a cellulose membrane (*Bio Industry*, 8(6), 412–420 (1991)).

In the above method, however, the cellulose membrane must be placed in an oxygen-free environment during the polymerization, and the cerium ions used as the polymerization initiator must be removed from the cellulose membrane, so the reaction conditions are unusually complex. In addition, since MPC tends to diffuse, it enters into the pores and reacts with the whole membrane, resulting in such problems as a decrease in membrane permeability, damage to the membrane by the cerium ions, a decrease in mechanical strength, non-uniform reaction, and irregularities in the suppression of thrombocyte adherence.

After taking into consideration biological safety, biological affinity, economical factors, chemical reactivity, and the like, the inventors arrived at the present invention.

The invention provides a method of producing a material bearing zwitterionic groups which comprises treating at least the surface of a substrate with a solution or dispersion, preferably solution, of a copolymer grafted with zwitterionic groups. The invention also relates to materials obtainable by this method.

The present invention further provides a material which comprises a substrate and fixed to at least a surface of the substrate, a carbohydrate derivative or functional derivative thereof grafted with zwitterionic groups.

Figure 1:
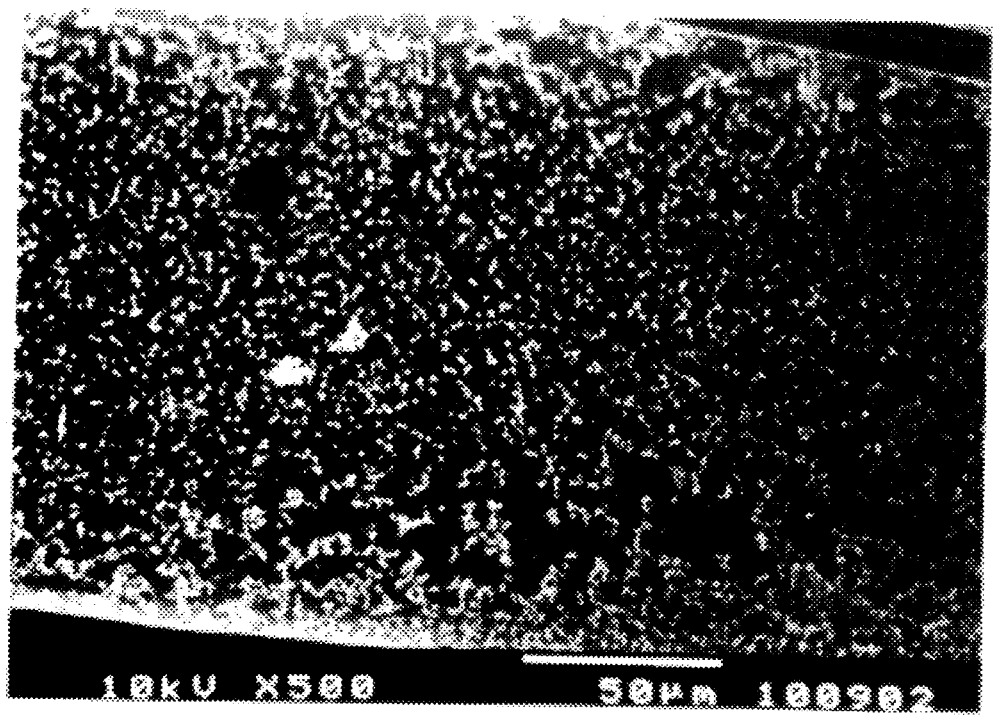
FIGS. 1–4 are microphotographs of surfaces of the membranes in accordance with Comparative Example 1, Example 16, Comparative Example 3 and Example 18, respectively.

The surface of the material treated with the grafted polymer may for example be a surface which is intended to come into direct contact with blood, either extra- or intra corporeally, i.e. it is a blood-contacting surface. Alternatively the surface may be one which comes into contact with another protein-containing fluid, such as biological fluid; in such cases treatment with the grafted polymer may lead to a material which exhibits a reduction in protein adsorption. Such materials are useful in contact lens (to reduce protein adsorption on the lens) and biomedical devices as well as blood-contact devices.

The invention therefore further provides a device such as a contact lens, biomedical device, blood-contacting device or filtration membranes which comprises a material according to the present invention as a fluid-contacting material for example as a blood contacting material or a material coming into contact with biological fluids and/or protein-containing solutions.

In one specific embodiment, the present invention provides:

an anti-thrombogenic regenerated cellulose membrane, which comprises a carbohydrate derivative or functional derivative thereof containing phosphorylcholine groups, which are fixed at least to the membrane surface of the regenerated cellulose membrane, which comes in contact with the blood; and a method for manufacturing an anti-thrombogenic regenerated cellulose membrane, in which a solution containing carbohydrate derivative or functional derivative thereof which contains phosphorylcholine groups is added to a regenerated cellulose membrane, the excess solution is then removed, and the above-mentioned derivatives are then fixed to the regenerated cellulose membrane.

As examples of zwitterionic groups which may be present in the cellulose material of the invention, there may be mentioned groups of the formula (I):

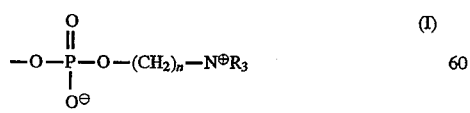

(I)

in which the groups R are the same or different and each is a straight or branched $C_1$-$C_4$ alkyl group; and
n is from 2 to 4.

In the groups of formula (I), all the R groups are preferably the same but compounds where the R groups are different are usable. Also preferred are those compounds where the R groups are straight chain alkyl groups, i.e., methyl, ethyl, n-propyl or n-butyl, most preferably methyl.

Most preferably all the groups R are methyl groups and n is 2, in which case the groups of formula (I) are phosphoryl choline groups.

The zwitterionic groups can be grafted to the polymer to produce the graft polymer using various well-known methods for polymer grafting.

Graft polymers containing zwitterionic groups may be obtained by grafting to the polymer, a compound containing a zwitterionic group and preferably a radical polymerisable, more preferably ethylenically unsaturated, compound containing a zwitterionic group. Radical initiated grafting to the polymer of such compounds provides polymerisation of the zwitterionic compound initiated by the graft. Such a graft-polymerisation reaction is preferably carried out in an aqueous solution system, using as an initiator a peroxide, or cerium ions, which allow radicals to form on the polymer.

Particular examples of polymerisable compounds containing a zwitterionic group are those of formula (II):

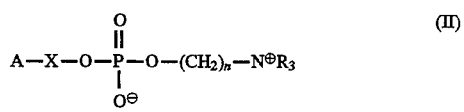

(II)

in which R and n are as defined in relation to formula (I);

A is a radical polymerisable group; and

X is an aryl group or a straight or branched $C_1$-$C_{20}$ alkylene group, optionally containing one or more carbon-carbon double or triple bonds, ether linkages or aryl groups; the aryl groups being unsubstituted or substituted by one or more $C_{1-4}$ alkyl groups.

Preferably X is a group of formula —$(CH_2)_a$—, —$(CH_2CH_2O)_b$—, —or —$(CH_2)_cAr(CH_2)_d$—, wherein a is from 1 to 20, e.g., 1 to 8, b is from to 1 to 20, e.g., 1 to 7, and c and d are the same or different and are from 0 to 5 and Ar is an aryl group, such as a para- or meta- (preferably para-) disubstituted phenyl group which is optionally further substituted by one or more $C_{1-4}$ alkyl groups, e.g., paradisubstituted phenyl (p—$C_6H_4$).

Particular examples of aryl-containing groups X are —$CH_2(p—C_6H_4)CH_2$—, —$CH_2(p—C_6H_4)$—, —(p—$C_6H_4)CH_2$—, and —(p—$C_6H_4)$—.

Preferably A is an ethylenically unsaturated radical polymerisable group, more preferably a vinyl-containing group, such a methacrylate, acrylate or styrene derived group. Groups of formula (IIA) and (IIB) provide particular examples of such groups. Groups of formula (IIA) are most preferred.

Groups of formula (IIA) are:

(IIA)

wherein $R^1$ is hydrogen or more preferably straight or branched $C_1$-$C_4$ alkyl, e.g., methyl, and Y is —O— or —$NR^2$— where $R^2$ is hydrogen or straight or branched $C_1$-$C_4$ alkyl or $R^2$ is a group:

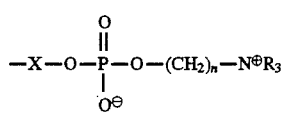

wherein X, R and n are as hereinbefore defined.

Groups of formula (IIB) are:

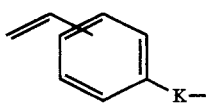

wherein:

K is a group $-(CH_2)_qOC(O)-$, $-(CH_2)_qC(O)O-$, $-(CH_2)_qOC(O)O-$, $-(CH_2)_qNR^3-$, $-(CH_2)_qNR^3C(O)-$, $-(CH_2)_qC(O)NR^3$, $-(CH_2)_qNR^3C(O)O-$, $-(CH_2)_qOC(O)NR^3-$, $-(CH_2)_qNR^3-C(O)NR^3-$, $-(CH_2)_qO-$, $-(CH_2)_qSO_3-$, or a valence bond and q is from 0 to 12 and $R^3$ is hydrogen or a $C_1$-$C_4$ alkyl group.

Where K is a group $-(CH_2)_qNR^3C(O)NR^3-$, the groups $R^3$ may be the same or different.

Preferably, in the groups of formula (IIB) K is a valence bond. Where K is a group then preferably q is from 1 to 6, more preferably 1, 2 or 3 and most preferably q is 1. When K is a group $-(CH_2)_qNR^3-$, $-(CH_2)_qNR^3C(O)-$, $-(CH_2)_qC(O)NR^3-$, $-(CH_2)_qNR^3C(O)O-$, $-(CH_2)_qOC(O)NR^3-$, or $-(CH_2)_qNR^3C(O)NR^3-$ then $R^3$ is preferably hydrogen, methyl or ethyl, more preferably hydrogen.

Of the compounds containing groups of formula (IIA) and (IIB), those containing groups of formula (IIA) are more preferred.

Most preferably the compound of formula (II) is 2(methacryloyloxy)-ethyl-2'(trimethylammonium) ethyl phosphate inner salt (MPC).

The concentration of groups of formula (I) graft-polymerised can be reduced by copolymersing with a diluent monomer. Thus the polymer is grafted with polymer chains comprising residues of a compound containing a group of formula (I) and optionally residues of diluent comonomer.

A diluent comonomer may be of any known conventional, radical polymerisable, preferably ethylenically unsaturated, type. A single diluent comonomer or alternatively more than one type of diluent comonomer may be used.

Examples of diluent comohomers include alkyl(alk) acrylate preferably containing 1 to 4 carbon atoms in the alkyl group of the ester moiety, such as methyl (alk)acrylate; a dialkylamino alkyl(alk)acrylate, preferably containing 1 to 4 carbon atoms in each alkyl moiety of the amine and 1 to 4 carbon atoms in the alkylene chain, e.g., 2-(dimethylamino)ethyl (alk) acrylate; an alkyl (alk) acrylamide preferably containing 1 to 4 carbon atoms in the alkyl group of the amide moiety; a hydroxyalkyl (alk)acrylate preferably containing from 1 to 4 carbon atoms in the hydroxyalkyl moiety, e.g., a 2-hydroxyethyl (alk)acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, (pentafluorophenyl)styrene.

It is to be understood that throughout the specification (alk)acrylate, (alk) acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth) acrylate, (meth)acrylic and (meth) acrylamide shall be understood to mean acrylate or methacrylate, acrylic or methacrylic and acrylamide or methacrylamide respectively.

Further diluents which may be mentioned specifically include alkylene anhydrides such as maleic anhydride or cyano-substituted alkylenes, such as acrylonitrile.

The present invention may be used to treat many known types as substrate, especially polymeric substrates and especially those used in manufacture of bio-medical apparatus, contact lenses and blood-contacting devices, such as hydroxy alkyl acrylate or alkacrylate, (e.g., methacrylate) hydrogels for example, hydroxyethyl-methacrylate (HEMA) hydrogels or hydroxyethyl methacrylate/ methacrylic acid (HEMA/MA) hydrogels, cellulose and cellulose derivatives such as Cuprophan, cellulose acetate and cellulose nitrate, polyvinyldifluoride (PVDF), polyamides (e.g., nylons), polyimides.

Other polymeric substrates which may be treated in accordance with the present invention include polyurethanes, polyimines and polyethersulphones.

The present invention is particularly applicable to the treatment of cellulose substrates.

The polymer to which the zwitterionic groups are grafted and which is used to treat the substrate may be selected from the same polymeric materials as those used as substrate, and is preferably selected for compatibility with the substrate. Preferably therefore the substrate and grafted polymer comprise the same type of polymer.

In one embodiment the polymer used to treat the substrate is a carbohydrate derivative or function derivative thereof, such as a cellulose derivative, a starch derivative, or a hydroxyl alkyl acrylate or alkacrylate polymer. Preferably a carbohydrate derivative or functional derivative thereof is used.

In addition, the present invention may be applied to the treatment of non-polymeric substrates such as silicon rubber and stainless steel, and also glass which preferably include a polymeric subbing layer. Subbing layers may also be included on polymeric substrate. Preferred materials for use as subbing layers include hydroxy (alk)acrylates, more preferably HEMA, and functionalised polyimines, for example halogenated polyethyleneimine silane.

The present invention will not be described in more detail, in relation to the treatment of cellulose membranes as substrates. However it will be appreciated that the particular details for treatment of the membranes may be equally applied to other substrates.

The regenerated cellulose is preferably a natural cellulose which has been modified, either chemically or physically, and then regenerated; examples include cellulose membranes regenerated by the copper ammonium method, vicose-rayon and cellulose ester saponification products. From the perspective of dialysis capacity and high safety confirmed by years of experience, however, the use of cellulose membrane regenerated by the copper ammonium method is preferred.

With respect to the shape of the regenerated cellulose, although products molded into the form of a flat membrane of a capillary membrane, or the like, can be used, the use of a capillary membrane is recommended. For example, a capillary membrane with a thickness of several μm to 60 μm, and a cross-section surface with an external diameter of 10 μm to several hundred μm, such as the membrane disclosed in Japanese Laid-Open Patent Applications 50-40168 and 59-204912, or the like, can be used.

Carbohydrates or functional derivatives thereof to which phosphorylcholine groups have been bonded directly or via several bonds can be used as the carbohydrate derivatives or functional derivatives thereof which contain zwitterionic groups.

The carbohydrates or functional derivatives thereof can be a natural product which has been modified, either chemically or physically, and then regenerated, or a synthetic product.

For example, glucose, xylose, fructose, ylulose or other monosaccharides, trehalose, saccharose, maltose, cellobiose, lactose or other disaccharides, raffinose, maltotriose, or other trisaccharides, xylan, amilose, glycogen, lenthinan, cellulose, dextran, pullulan, agarose, mannane, inulin, chitin, polygalaxylonic acid, polyribosphosphate, or other homopolysaccharides, chondroitin, hyaluronic acid, heparin, arabic gum, alginic acid, or other hetropolysaccharides, can be used. Ribopolysaccharides, glycoproteins, glucosides, or the like, can also be used.

In addition, methylcellulose, cellulose acetate, nitrocellulose or the like, can of course be used as a functional derivatives of the above-mentioned carbohydrates. From the perspective of the affinity of the regenerated cellulose membrane, cellulose should be used, and when water is used as the solvent to treat the regenerated cellulose membrane, cellulose with a degree of polymerization of 3 to 50 should be used, and preferably cellulose with a degree of polymerization of 5 to 10.

The solvent used (hereinafter "the added solvent") when the carbohydrate derivatives or functional derivatives thereof which contain phosphorylcholine groups (hereinafter, the above derivatives will be called "polymers") are added to the regenerated cellulose membrane should be a solvent which uniformly dissolves the polymers and which readily allows for impregnation and application of the polymers to the membrane surface. As mentioned below, any solvent that can dissolve the above-mentioned polymers can basically be used in the present invention.

A suitable solvent must be selected taking into consideration whether it can be readily removed, whether it is safe in case small quantities thereof remain, and the like. In the present invention, it is preferable to use water, methanol, ethanol or other low-grade alcohols, acetone or dimethylformamide, or mixtures of these solvents with water, as such a solvent.

The polymers dissolved in the above-mentioned added solvents exhibit satisfactory effects at low concentrations. If [the polymers] are added at high concentrations, it is difficult to obtain uniformity, resulting in unbalanced properties, as well as the problem of polymer shedding during operation, and is therefore undesirable. In the present invention, the polymer concentration should be within a range of 0.005 to 5 weight/volume % (hereinafter "w/v%"), and preferably within a range of 0.01 to 1 w/v%.

Such a low polymer concentration can be used in the present invention because of the low fixed quantity of the polymer, so that beneficial effects in improving the anti-thrombogenicity are brought about without adversely affecting the dialysis capacity [of the membrane]; for example, the objective of the present invention can be satisfactorily accomplished, even when the quantity of the fixed polymer is several µg/cm$^2$ with respect to the regenerated cellulose membrane.

The quantity of the fixed polymer can generally be calculated by decomposing the polymer and the regenerated cellulose membrane to which the polymer was fixed using perchloric acid, and by determining the quantity using organic phosphorus.

In implementing the present invention the quantity of the fixed polymer should be within the range of 1 to 100 µg/cm$^2$, and preferably within the range of 5 to 50 µg/cm$^2$.

For example, when MPC graft cellulose is fixed to a regenerated cellulose membrane as a polymer, the membrane surface is then measured using ESCA, and the percentage of the carbon and phosphorus atoms is calculated, so that the molar fraction {R(mol %)} of these atoms, with respect to the glucose units of the cellulose of the phosphorylcholine groups on the membrane surface of the regenerated cellulose membrane, can be obtained using the following formula.

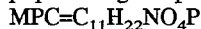

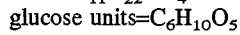

c: percentage of carbon atoms (mol %)
p: percentage of phosphorus atoms (mol %)
MPC=$C_{11}H_{22}NO_4P$
glucose units=$C_6H_{10}O_5$ R should be within the range of 0.5 to 50 mol %, and preferably within the range of 3 to 40 mol %.

The polymer can be fixed to the regenerated cellulose membrane using the following method.

First, the polymer is dissolved in the added solvent, and the polymer solution thus obtained is added to the cellulose membrane by means of impregnation, application, or another method. Next, the excess polymer solution is removed from the membrane surface using such methods as centrifugation, suction, or the like. Unless the drainage process is thoroughly conducted, there is some danger that unbalanced properties will result, and the polymer may shed during use. After the draining, the polymer is fixed by removing the added solvent.

The added solvent can be removed, if the solvent is volatile, using such conventional methods as vacuum drying, air drying, heat drying, or the like, whereas in the case of a solvent having a relatively high boiling point, the added solvent can be removed using such methods as rinsing, using a solvent which does not contain the polymer as needed, then rinsing using a volatile organic solvent which has good compatibility with the solvent, and drying using such methods as those mentioned above. In addition, if the solvent is soluble in water, the regenerated cellulose membrane can be rinsed with water which is poured into the dialyzer.

To further enhance the fixing uniformity, a process which involves adding the polymer solution to the membrane surface, draining and fixing the polymer can be repeated. The heat treatment described below can also be included in the repetition.

After removing the added solvent, a heat treatment can be conducted. Such a heat treatment prevents shedding of the polymer and is effective in yielding higher anti-thrombogenicity. The heat treatment should be conducted at a temperature range of 50° to 150° C. and preferably 70° to 130° C.

Either dry heating or steam heating can be used as the method of heat treatment, and such methods as far infra-red heating are also effective. The time period of the heat treatment should be established in accordance with the results to be obtained, but usually it ranges between less than a minute to several hours, and preferably from one minute to one hour. If steam sterilization is conducted, satisfactory effects can be obtained without further conducting the above-mentioned heat treatment. The fixing should be such that no shedding of the polymer occurs during the operation, and it is preferably to fix the polymer to the cellulose membrane in more than one site.

The above-mentioned manufacturing method can be similarly applied whether the membrane surface which comes in contact with the blood, and to which the polymer should be attached, is the internal surface or the external surface of a capillary membrane or the like. The above-mentioned manufacturing method should be applied especially if the added solvent can bring about deformation of the regenerated cellulose membrane while the regenerated cellulose membrane is inserted into the dialyzer; in such a case, the added solvent should not be removed by drying, but should be removed by rinsing with water.

It will equally be appreciated that the above method can be adapted, using conventional methods, to the manufacture of other devices which come into contact with fluids such as blood, other biological fluids or protein-containing solutions. In particular the materials of the invention may be used as or incorporated in implants, prostheses, membranes such as filtration membranes, catheters, contact lenses and other devices which contact such fluid extra- or intra-corporeally. Preferences expressed above in relation to cellulose membranes may in general be applied to such other materials, particularly such materials which comprises a carbohydrate derivative on functional derivative thereof as graft polymer and/or a cellulose substrate.

BRIEF DESCRIPTION OF THE DRAWINGS

FIG. 1 shows an SEM photograph of the inner surface of an untreated cellulose capillary membrane after whole blood was passed inside for 60 minutes, in accordance with Comparative Example 1.

Figure 2:
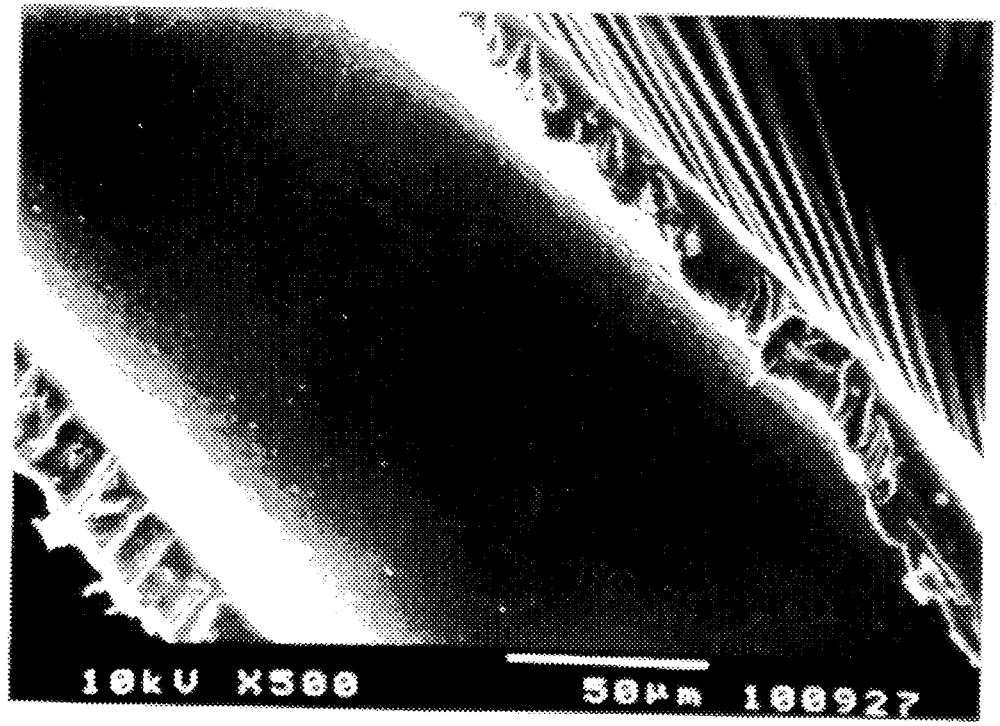

FIG. 2 shows an SEM photograph of the inner surface of a cellulose capillary membrane treated in accordance with the invention after whole blood was passed inside for 60 minutes in accordance with Example 16.

Figure 3:
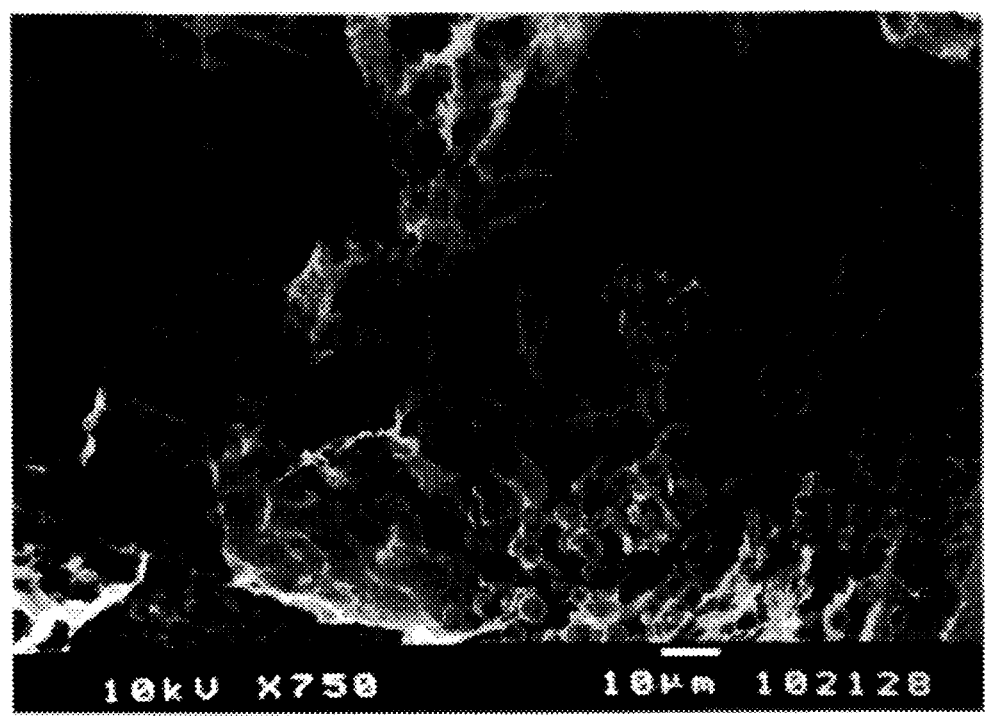

FIG. 3 shows an SEM photograph of the inner surface of an untreated cellulose capillary membrane after whole blood was passed inside in accordance with Comparative Example 3.

Figure 4:
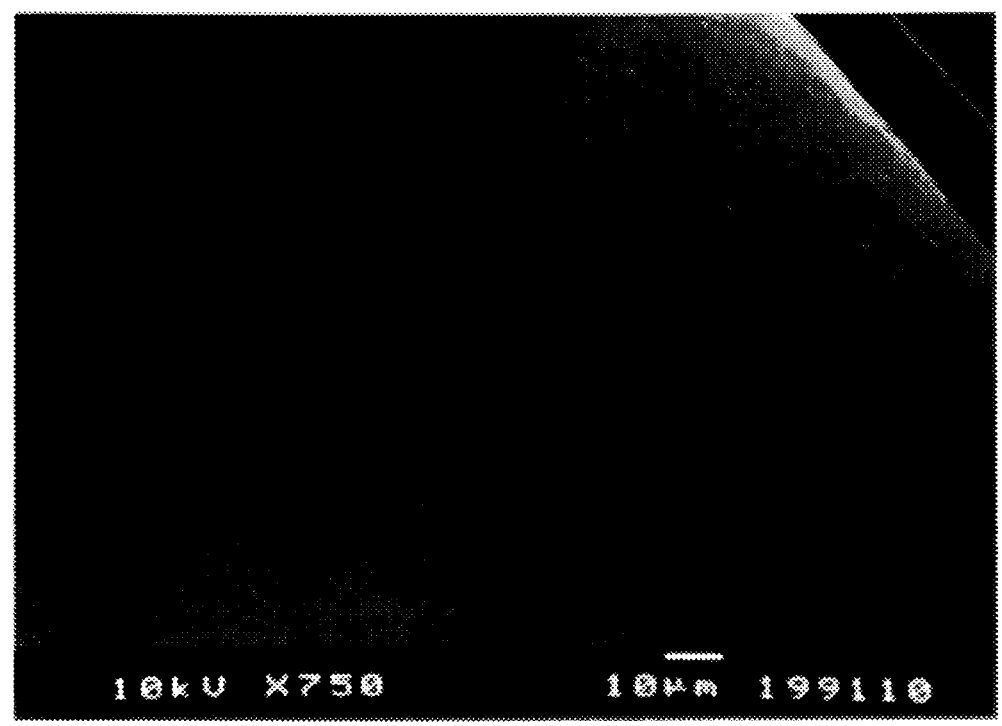

FIG. 4 shows an SEM photograph of the inner surface of a cellulose capillary membrane treated in accordance with the invention after whole blood was passed inside in accordance with Example 18.

The present invention will be further illustrated by the following Examples.

EXAMPLES

The measurements cited in the following examples were conducted using the following methods.

In addition, the measurements cited in the following practical examples were each conducted using the following methods.

(1) The quantity of the grafted MPC 0.5 wt. % aqueous solution of MPC-graft cellulose was diluted 800 fold using water, 50 µL thereof was put in a test tube and dried. 260µL of a commercially-available perchloric acid (70%) was added to the product, and heating was conducted at 180° C. for 20 minutes. After cooling, 1.90 mL distilled water, 0.40 mL of 1.25 wt. % ammonium molybdate, and 0.4 mL of 5 wt. % L-ascorbic acid was added, and heating was further conducted at 100° C. for five minutes. The light absorption (797 nm) of the solution, which was colored blue, was measured, and the phosphorus was determined from a calibration curve using sodium hydrogenphosphate. Using these values, the quantity of the MPC grafted was determined in wt. % units, with respect to the MPC-graft cellulose of the MPC.

(2) The quantity of the polymer fixed

A 1 $cm^2$ piece of cellulose membrane to which MPC-graft cellulose (polymer) was fixed was cut at approximately 2 mm and inserted into a test tube. The phosphorus [content] was measured in the same manner as in (1), and the quantity of polymer on the cellulose membrane (units: $\mu g/cm^2$) was determined from the values measured and from the quantity of the MPC grafted.

(3) The molar ratio of the phosphorylcholine group (PC)

The well-dried membrane surface of the cellulose membrane to which the MPC-graft cellulose (polymer) was fixed as measured using ESCA (esca-750, manufactured by Shimadzu K.K.), the percentage of carbon and phosphorus atoms was determined, and the molar fraction [R(mol %] of these atoms, with respect to the glucose units of the cellulose of the phosphorylcholine groups, on the membrane surface of the regenerated cellulose membrane was obtained using the following formula.

$$R = p/\{p + (c - 11p)/6\}$$

c: percentage of carbon atoms (mol %)
p: percentage of phosphorus atoms (mol %)
MPC=$C_{11}H_{22}NO_6P$
glucose units=$C_6H_{10}O_5$

EXAMPLE 1

10 g cellulose powder (Cellulose Native for TLC, manufactured by Merk Co.) was dispersed in 38 mL acetic anhydride and 38 mL frozen acetic acid, and 4 mL concentrated sulfuric acid was added therein. The mixture was stirred for one hour at 50° C., yielding a transparent liquid. The liquid was added dropwise into acetone and allowed to re-precipitate, the low molecular weight compounds were removed by filtration, and vacuum drying was conducted, yielding 9.5 g acetylcellulose.

50 mL of 1N aqueous solution of sodium carbonate and 100 mL of 3N aqueous solution of sodium hydroxide were added to 2.5 g of the above acetylcellulose, stirred, and subjected to deacetylation. Hydrochloric acid was added to the reaction solution to neutralize it, the solution was introduced into the dialysis membrane, dialysis was conducted in water for three days to remove the low molecular weight substances, and a water-soluble cellulose was thus obtained. A portion of the solution was collected and dried by heat, and the weight concentration of the cellulose as measured; the cellulose was diluted by water, and 0.5 wt. % solution was produced.

0.6 g cerium (IV) ammonium nitrate and 10 mL of 0.1N nitric acid were added to 10 mL of the 0.5 wt. % water-soluble cellulose aqueous solution. In addition, 0.9 g 2-methacryloyl phosphorylcholine (MPC) was added, and the resulting solution was placed under argon for ten minutes. The container was sealed, stirring was conducted for one hour at 40° C., and graft polymerization was conducted.

After the end of the reaction, the solution was introduced into the dialysis membrane, dialysis was conducted using water, and the MPC-graft cellulose was thus purified. The quantity of the MPC grafted to the cellulose was 8.0 wt. %.

EXAMPLES 2 TO 5

Reactions were conducted in the same manner as in Practical Example 1, except for the quantities of the MPC used, and MPC-graft cellulose was obtained. The results are shown in Table 1.

TABLE 1

Synthesis results of MPC-graft cellulose

|  | MPC(g) | Quantity of grafted MPC (wt %) |
|---|---|---|
| Example 2 | 1.2 | 11.3 |
| Example 3 | 1.8 | 17.4 |
| Example 4 | 2.4 | 23.8 |
| Example 5 | 3.0 | 37.5 |

EXAMPLES 6 TO 9

A 0.5 wt. % MPC-graft cellulose (hereinafter "polymer") aqueous solution was passed, at a flow rate of 5 mL/minute, through the interior of a module (effective length: 8 cm) comprising 100 regenerated cellulose capillary membranes (internal diameter 200μm) manufactured using the copper ammonium method. The module was allowed to stand for ten minutes with its inside filled with the polymer solution, the solution was extracted using air, and vacuum drying was immediately conducted for three hours at room temperature. The quantity of the polymer fixed and the PC molar ratio are shown in Table 2.

TABLE 2

Results of fixing cellulose capillary membranes using a 0.5 wt % MPC-graft cellulose aqueous solution

|  | Polymer used | Quantity of fixed polymer (μg/cm$^2$) | Molar ratio of PC (%) |
|---|---|---|---|
| Example 6 | Example 2 | 8.6 | 15.4 |
| Example 7 | Example 3 | 6.3 | 7.2 |
| Example 8 | Example 4 | 12.6 | 35.0 |
| Example 9 | Example 5 | 10.4 | 23.8 |

EXAMPLES 10 TO 12

The polymer was fixed to the capillary membranes in the same manner as in Example 6, except that the polymer concentration was 1.0 wt. % and the polymer aqueous solution was passed through the capillary membrane at a flow rate of 10 mL/minute. The results are shown in Table 3.

TABLE 3

Results of fixing cellulose capillary membranes using a 1.0 wt % MPC-graft cellulose aqueous solution

|  | Polymer used | Quantity of fixed polymer (μg/cm$^2$) | Molar ratio of PC (%) |
|---|---|---|---|
| Example 10 | Example 1 | 8.9 | 10.5 |
| Example 11 | Example 3 | 10.2 | 26.0 |
| Example 12 | Example 5 | 12.7 | 39.0 |

EXAMPLES 13 THROUGH 16

The same regenerated cellulose capillary membrane module was used as in Example 6 (total membrane surface area: 50 cm$^2$). Fresh blood was drawn from the carotid artery of a rabbit, using sodium citrate (0.38%) as an anticoagulant, and passed through the membrane for 60 minutes at a flow rate of 0.5 mL/minute. The insides of the capillaries were then rinsed using physiological saline water, and lastly, they were filled with a physiological saline solution containing 25% glutaraldehyde and were allowed to stand for two hours. The inside was replaced with pure water so and freeze-dried.

Following metal-vapor deposition, the inside surfaces of the capillary membrane were observed using a scanning electron microscope (SEM), and the number of thrombocytes which had adhered as counted. The results are shown in Table 4.

COMPARATIVE EXAMPLES 1 AND 2

The same procedures as in Practical Examples 13 through 16 were used to treat an untreated cellulose capillary membrane and a ethylene-vinyl alcohol copolymer capillary membrane, and the number of thrombocytes which had adhered was counted. The results are shown in Table 4.

The SEM photographs corresponding to Comparative Example 1 and Example 13 are shown in FIGS. 1 and 2.

TABLE 4

Experimental results of thrombocytes adhering to a cellulose capillary membrane to which an MPC-graft cellulose was fixed

|  | Capillary membrane used | Number of adhered thrombocytes (thrombocytes/mm$^2$) |
|---|---|---|
| Example 13 | Example 6 | 0 |
| Example 14 | Example 8 | 0 |
| Example 15 | Example 11 | 0 |
| Example 16 | Example 12 |  |
| Comparative Example 1 | Untreated cellulose capillary membrane | 7.98 × 10$^4$ |
| Comparative Example 2 | Ethylene-vinyl alcohol copolymer capillary membrane | 8.38 × 10$^4$ |

EXAMPLES 17 AND 18

The same regenerated cellulose module (total membrane surface area: 50 cm$^2$) as in Example 6 was connected to a blood circuit which was created between the carotid artery and the jugular vein of a rabbit, and the blood flow was regulated to a flow rate of 2 mL/minute. No anticoagulants were administered, and the time period until the blood coagulated inside the capillary membrane was measured.

After the end of the experiment, the inside surfaces of the capillary membranes were observed by SEM using he same procedures as in Examples 13 through 16. The results are shown in Table 5.

COMPARATIVE EXAMPLES 3 AND 4

The same procedures as in Examples 17 and 18 were conducted using the untreated cellulose capillary membrane and the ethylene-vinyl alcohol copolymer capillary membrane to measure the clotting time. The results are shown in FIG. 5.

The SEM photographs corresponding to Comparative Example 3 and Example 18 are shown in FIGS. 3 and 4.

TABLE 5

Whole blood clotting time of a cellulose capillary membrane to which an MPC-graft cellulose was fixed

|  | Capillary membrane used | Clotting time |
|---|---|---|
| Example 17 | Example 9 | >60 minutes |
| Example 18 | Example 12 | >60 minutes |
| Comparative Example 3 | Untreated cellulose capillary membrane | 40 minutes |
| Comparative Example 4 | Ethylene-vinyl alcohol copolymer capillary membrane | 45 minutes< |

Examples 13 to 18 thus demonstrate considerably improved anti-thrombogenicity compared to untreated cellulose membranes or ethylene-vinyl alcohol copolymer capillary membranes.

EXAMPLE 19

The mass transfer coefficients of urea and creatinin were each measured. Specifically, a module comprising a bundle of 100 regenerated cellulose capillary membranes (internal diameter: 200 μm), fixed at both ends using an adhesive, was subjected to polymer fixing under the same conditions as in Examples 8, 9 and 12. The modules were immersed in 30L water which was vigorously stirred, and a mixed aqueous solution of 1,000 mg/L urea and 200 mg/L creatinin (original solution) was passed inside.

After 60 minutes, the urea and creatinin concentrations (Bout) of the solution at the module exit were measured, and the mass transfer coefficients {K(cm/S)} were calculated using the following formula. The results are shown in Table 6.

Formula 3

K=(flow rate (mL/s.)/membrane surface area (cm$^2$)×ln (concentration of original solution/Bout)

TABLE 6

Mass transfer coefficients of cellulose capillary membranes to which an MPC-graft cellulose was fixed

| Treatment conditions of capillary membrane | Mass transfer coefficients (× 10$^{-4}$cm/s.) | |
|---|---|---|
| Example 8 | 9.8 | 7.0 |
| Example 9 | 10.5 | 6.9 |
| Example 12 | 10.0 | 7.3 |
| Untreated cellulose capillary membrane | 10.2 | 7.2 |

Thus the permeation performance of the membrane in accordance with the invention is maintained for practical purposes compared to an untreated membrane.

EXAMPLE 20

A 1250 cm$^2$ piece of a regenerated cellulose capillary membrane, to which a polymer was fixed under the same conditions as in Examples 8, 11 and 12, was cut to 2 mm and put into a three-necked flask; 100 mL water was added, and extraction was conducted for five hours at 40° C. The capillary membrane was filtered, the extraction solution was freeze-dried and then dissolved in water again, and made up to 10 mL. The phosphorus and cerium in the above solution were determined, but were not extracted. The phosphorus was determined using the method cited for measuring the quantity of the above-mentioned (1) grafted MPC. The cerium was determined using a plasma emission analysis (ICPA-575, manufactured by NGA Co.).

We claim:

1. A method of producing a material bearing zwitterionic groups, comprising the step of treating the surface of a substrate with a solution or dispersion of a polymer grafted with zwitterionic groups, wherein the graft polymer is obtained by graft-polymerization on the polymer of a compound of formula (II)

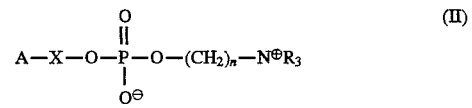

in which the groups R are the same or different and each is a straight or branched $C_3$-$C_4$ alkyl group;

n is from 2 to 4;

A is a radical polymerizable group; and

X is an aryl group or a straight or branched $C_1$-$C_{20}$ alkylene group; the aryl groups being unsubstituted or substituted by one or more $C_{1-4}$ alkyl groups; and the treating step comprises application of the solution or dispersion to the surface of the substrate, followed by removal of excess solution or dispersion and removal of solvent to fix the polymer at said surface.

2. A method according to claim 1 in which each R represents a methyl group and n is 2.

3. A method according to claim 2 in which the graft polymer is obtained by grafting of 2(methacryloyloxy)-ethyl-2'(trimethylammonium) ethyl phosphate inner salt.

4. A method according to any one of the preceding claims in which the polymer to which zwitterionic groups are grafted and the substrate comprise the same polymer.

5. A method according to claim in which the graft polymer comprises a carbonhydrate.

6. A method according to claims 5 in which the carbohydrate is cellulose.

7. A method according to claim 1 which provides from 1 to 100 μg of graft polymer per cm$^2$ of substrate.

8. A method according to claim 1 which comprises fixing the graft polymer to the substrate by heat treatment at a temperature from 50 to 150° C.

9. A membrane coated by a graft polymer obtained by graft-polymerization on a polymer of a compound of formula (II)

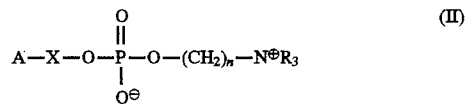

in which the groups R are the same or different and each is a straight or branched $C_1$-$C_4$ alkyl group;

n is from 2 to 4;

A is a radical polymerizable group; and

X is an aryl group or a straight or branched $C_1$-$C_{20}$ alkylene group, the aryl group being unsubstituted or substituted by one or more $C_{1-4}$ alkyl groups.

10. A membrane according to claim 9 in which the membrane is a regenerated cellulose membrane.

11. A membrane according to claim 9 in which the membrane is a blood contacting membrane, a filtration membrane or a biomedical device.

12. A contact lens coated by a graft polymer obtained by graft-polymerization on a polymer of a compound of formula (II)

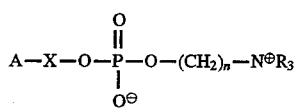

(II)

in which the groups R are the same or different and each is a straight or branched $C_1$-$C_4$ alkyl group;

n is from 2 to 4;

A is a radical polymerizable group; and

X is an aryl group or a straight or branched $C_1$-$C_{20}$ alkylene group, the aryl groups being unsubstituted or substituted by one or more $C_{1-4}$ alkyl groups.

13. A method according to claim 5 in which the graft polymer is formed from a compound selected from the group consisting of glucose, xylose, fructose, xylulose, trehalose, saccharose, maltose, cellobiose, lactose, raffinose, maltotriose, xylan, amylose, glycogen, lenthinan, cellulose, dextran, pullulan, agarose, mannane, inulin, chitin, polygalaxylonic acid, polyribosphosphate, chondroitin, haluronic acid, heparin, gum arabic, alginic acid, ribopolysaccharides, glycol proteins, glucosides, methylcellulose, cellulose acetate and nitro cellulose.

14. A method according to claim 5 in which said carbohydrate is cellulose having a degree of polymerization of 3–50.

15. A method according to claim 5 in which said carbohydrate is cellulose with a degree of polymerization of 5–10.

16. A method according to claim 1 in which said solution is in a solvent selected from the group consisting of water, alcohols, acetone, dimethylformamide and mixtures thereof.

17. A method according to claim 1 in which said solution is in a solvent comprising water.

18. A method according to claim 1 in which said solution is in a solvent consisting of water.

19. A method according to claim 1 in which the concentration of graft polymer in said solution or dispersion is in the range 0.005 to 5.0 weight/volume percent.

20. A method according to claim 1 in which the concentration of graft polymer in said solution or dispersion is in the range 0.01–1.0 weight/volume percent.

21. A method according to claim 1 in which the solvent is removed by vacuum drying.

22. A method according to claim 1 in which, after removal of the solvent, heat treatment is effected by heating the coated substrate at a temperature in the range of 50°–100° C.

23. A method according to claim 1, in which X contains one or more carbon-carbon double or triple bonds, ether linkages or aryl groups.

24. A membrane according to claim 9 in which X contains one or more carbon-carbon double or triple bonds, ether linkages or aryl groups.

25. A contact lens according to claim 12 in which X contains one or more carbon-carbon double or triple bonds, ether linkages or aryl groups.

26. A method according to claim 18 in which the concentration of graft polymer in said solution is in the range of 0.01–1.0 weight/volume percent and said solvent is removed by vacuum drying.

* * * * *